United States Patent [19]

Hintz

[11] 4,163,026
[45] Jul. 31, 1979

[54] PRODUCTION OF TETRABUTYLHEXAMETHYLENEDIAMINE BY REDUCTIVE ALKYLATION OF HEXAMETHYLENEDIAMINE WITH BUTYRALDEHYDE

[75] Inventor: Harold J. Hintz, Riverview, Mich.

[73] Assignee: Monsanto Company, St. Louis, Mo.

[21] Appl. No.: 832,301

[22] Filed: Sep. 12, 1977

[51] Int. Cl.$^2$ ............................................. C07C 85/08
[52] U.S. Cl. ................................................. 260/583 P
[58] Field of Search ............ 260/583 P, 583 R, 585 C

[56] References Cited

U.S. PATENT DOCUMENTS 2,317,757   4/1943   Graf .............................. 260/585 C X
2,373,705   4/1945   Olin et al. ......................... 260/583 R
3,707,563   12/1972  Glassboro ......................... 260/583 P

OTHER PUBLICATIONS

Mignonac et al., "Comptes Rendus", vol. 172, pp. 223-226 (1921).

Primary Examiner—Winston A. Douglas
Assistant Examiner—John Doll
Attorney, Agent, or Firm—Thomas Y. Awalt, Jr.

[57] ABSTRACT

Tetrabutylhexamethylenediamine is produced from butyraldehyde and hexamethylenediamine by continuously reacting controlled amounts of butyraldehyde with hexamethylenediamine in the presence of a platinum or palladium catalyst.

7 Claims, No Drawings

PRODUCTION OF TETRABUTYLHEXAMETHYLENEDIAMINE BY REDUCTIVE ALKYLATION OF HEXAMETHYLENEDIAMINE WITH BUTYRALDEHYDE

BACKGROUND OF THE INVENTION

A. Scope of the Invention

This invention relates to the production of tetrabutylhexamethylenediamine from butyraldehyde and hexamethylenediamine. Tetrabutylhexamethylenediamine is useful as an intermediate for the production of quaternary ammonium salts which in turn may be used as directive salts in the production of adiponitrile from acrylonitrile by electrohydrodimerization.

B. The Prior Art

The manufacture of amines by reaction of aliphatic aldehydes with aminating agents such as ammonia or aliphatic amines and hydrogen is well known. The reaction was discovered by Mignonac and reported in "Comptes Rendus", Volume 172, page 223. In accordance with this general process, as developed in Mignonac et al., the aminating agent is mixed with an aldehyde or ketone in the presence of a hydrogenation catalyst and the mixture is subjected in liquid phase, under the pressure of hydrogen, to a temperature above the minimum reaction temperature at which the desired condensation reaction occurs, and below the temperature of decomposition of the desired amine. In most cases, a mutual solvent, such as a monohydric primary, secondary or tertiary alcohol, a polyhydric alcohol or water, was employed in order to facilitate contact of the reactants or otherwise promote the reaction, although the presence of such a mutual solvent was not in all cases considered necessary.

In U.S. Pat. No. 2,373,705, refinements on the Mignonac process, in order to improve the very low yields and conversions attained, involved the treatment of the reactants in the liquid phase under an atmosphere of hydrogen. Any hydrogenation catalyst was reported useful according to this invention, but the Raney nickel catalyst was distinctly preferred. By-product formation was recognized as a problem. High pressures were believed to be required to maintain the reactants and products of the reaction in the liquid phase. Various amines were obtained, the highest of reported purity being the monopropylamine of Example 2, but most of the products represented conversions of no greater than about 50% (Examples 1 and 3).

Particularly in view of the current industrial need for adiponitrile as an intermediate for chemical and textile production, a practical and efficient process for the production of tetrabutylhexamethylenediamine from butyraldehyde and an aminating agent would represent a significant advance in the art.

SUMMARY OF THE INVENTION

According to the present convention, tetrabutylhexamethylenediamine is produced from butyraldehyde and hexamethylenediamine by continuously reacting controlled amounts of butyraldehyde with hexamethylenediamine in the presence of a platinum or palladium catalyst at a pressure of 300–500 pounds per square inch gauge (200–341 kg/cm$^2$) and a temperature of 70°–90° C.

An advantage of this invention is that by-products, characteristic of amination, are avoided.

Another advantage of this invention is that surprisingly high yields of the pure tetrabutylhexamethylenediamine are obtained.

Yet another advantage of this invention is that reaction pressures of the order taught in U.S. Pat. No. 2,373,705, which are expensive and impractical to maintain in a commercial process, are not required and preferably avoided.

DESCRIPTION OF THE PREFERRED EMBODIMENTS

The reactants are pure or nearly pure butyraldehyde and hexamethylenediamine. As indicated in U.S. Pat. No. 2,373,705, with respect to any manufacture of amines by reaction of aliphatic aldehydes with aminating agents, by-product formation is avoided by avoiding the presence of significant amounts of the aldehyde in the reaction mixture in contact with the aminating agent. Two equivalents of the butyraldehyde react instantly with hexamethylenediamine to form a bis-imine intermediate which must be hydrogenated for further alkylation to occur. Excesses of the butyraldehyde self condense in an aldol-type reaction catalyzed by hexamethylene diamine or imine intermediates. If the four required equivalents of butyraldehyde are added to hexamethylenediamine in a time during which only two can react in the desired manner before hydrogenation has taken place, it is apparent that excesses of butyraldehyde can cause excessive unwanted side reaction. It is therefore desirable to introduce the butyraldehyde to the hexamethylenediamine under reducing conditions so that the imine intermediates will by hydrogenated as they are formed—in controlled amounts.

The desired reaction is represented by the following equation:

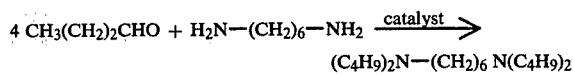

By-product formations to be avoided are as shown below:

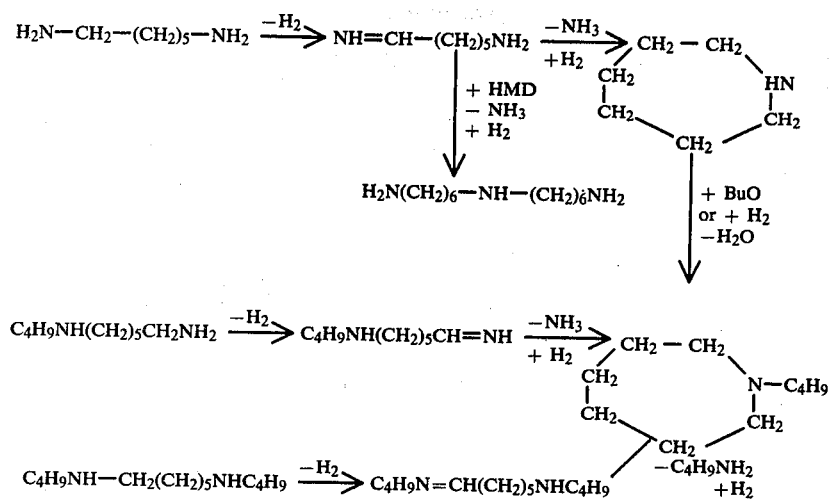

As shown by the Examples, the reactants may or may not be dissolved in a solvent. Preferably the solvent is not employed.

I have discovered that using a catalyst containing platinum or palladium under the conditions described leads to surprising improvements over prior art processes. Either or both supported on carbon are preferred.

A strong competitive reduction of butyraldehyde to butanol is not retarded significantly by reduction of temperature or pressure; and differences in butyraldehyde feed-rates apparently have very little affect.

The yields of tetrabutylhexamethylenediamine may be run even higher than those shown at the examples but only at the expense of impractical excesses of butyraldehyde.

While pressures of 300–500 psig (200–341 kg/cm²) have been specified, pressures of about 500 psig (341 kg/cm²) are preferred.

A temperature range of 70°–90° C. has been exemplified, but the preferred temperature is 80°–90° C.

EXAMPLES 1–5

Two milliliters per minute of 28.8 grams of butyraldehyde in 90 milliliters of ethanol were fed into a reactor containing 11.6 grams of hexamethylenediamine (HMD) in 75 milliliters of ethanol and the catalyst type shown. Conditions of pressure and temperature are as indicated. By Pt/C is meant platinum supported by carbon and by Pd/C is meant palladium supported by carbon. The reaction products, characterized as butanol (BuOH), N,N,N'-tributylhexamethylenediamine (3BHMD), tetrabutylhexamethylenediamine (TBHDM) and N,N,N'-tributyl-N'-(2-ethylhexyl)hexamethylenediamine (TBHMD+1), were as shown by the following table.

TABLE 1

| Example | Wt. Catalyst (g) | Catalyst type | Press. (psig) | Press. (kg/cm²) | Temp. (°C.) | % BuOH | % 3BHMD | % TBHMD | % TBHMD+1 |
|---|---|---|---|---|---|---|---|---|---|
| 1 | 5.0 | 5% Pt/C | 500 | 341 | 80–90 | 8.9 | 7.1 | 82.2 | — |
| 2 | 5.0 | 5% Pt/C | 500 | 341 | 80–90 | 10.5 | 3.8 | 76.0 | — |
| 3 | 5.0 | 10% Pd/C | 500 | 341 | 90 | 6.9 | 0.3 | 88.1 | — |
| 4 | 1.0 | 10% Pd/C | 250 | 170 | 90 | 0.5 | 4.1 | 83.5 | 4.0 |
| 5 | 0.1 | 10% Pd/C | 250 | 170 | 90 | — | 23.0 | 15.0 | 4.8 |

EXAMPLES 6–16

Butyraldehyde was fed into a reactor at two milliliters per minute. The catalyst was 10% palladium/carbon employed in the amount indicated. No solvent was employed. The amounts of hexamethylenediamine in the reactor were as indicated. All reactions were conducted at 100° C. and 500 psig (341 kg/cm²).

TABLE 2

| Example | Wt. Catalyst (g) | Wt. HMD | Wt. BuO | % BuO | % BuOH | % 3BHMD | % TBHMD | % TBHMD+1 |
|---|---|---|---|---|---|---|---|---|
| 6 | 2.0 | 34.8 | 108 | 1.66 | 14.00 | 0 | 79.75 | — |
| 7 | 1.0 | 34.8 | 95 | 7.72 | 0.35 | 0 | 91.00 | 0.24 |
| 8 | 1.5 | 52.2 | 142.5 | 26.23 | 1.42 | 0 | 76.30 | 1.26 |
| 9 | 1.5 | 52.2 | 142.5 | 9.70 | 0.76 | 0 | 87.89 | 0.73 |
| 10 | 1.5 | 52.2 | 142.5 | 7.00 | 0.77 | 0 | 91.32 | 0.29 |
| 11 | 1.5 | 52.2 | 142.5 | 3.91 | 0.62 | 0 | 94.59 | 0.30 |
| 12 | 1.5 | 52.2 | 142.5 | 0 | 0 | 2.17 | 90.85 | 0.36 |
| 13 | 1.5 | 52.2 | 142.5 | 7.20 | 1.01 | 6.19 | 82.41 | 0.68 |
| 14 | 1.5 | 52.2 | 142.5 | 21.10 | 1.42 | 0.61 | 76.20 | 0.24 |
| 15 | 7.5 | 174 | 432 | 0.33 | 5.86 | 0 | 91.44 | 1.29 |

TABLE 2-continued

| Example | Wt. Catalyst (g) | Wt. HMD | Wt. BuO | % BuO | % BuOH | % 3BHMD | % TBHMD | % TBHMD+1 |
| --- | --- | --- | --- | --- | --- | --- | --- | --- |
| 16 | 7.5 | 174 | 432 | 0.12 | 0.07 | 1.68 | 87.89 | 4.62 |

EXAMPLES 17-19

The following reactions were conducted at a butyraldehyde feed rate of 0.5 milliliters/min. (for examples 17 and 18) and two milliliters/min. (for example 19). The temperature was 100° C. and the pressure was 500 psig (341 kg/cm²) of H₂.

TABLE 3

| Example | Wt. Catalyst (g) | Wt. HMD | Wt. BuO | % BuO | % BuOH | % 3BHMD | % TBHMD | % TBHMD+1 |
| --- | --- | --- | --- | --- | --- | --- | --- | --- |
| 17 | 0.5 | 34.8 | 95 | 0 | 1.80 | 0 | 94.89 | 0.92 |
| 18 | 0.5 | 34.8 | 95 | 0.16 | 3.52 | 0 | 93.22 | 0.88 |
| 19 | 15.0 | 174 | 432 | 1.64 | 1.19 | 0 | 92.87 | 2.53 |

EXAMPLES 20-28

100° C. and 500 psig (341 kg/cm²) H₂. The butyraldehyde feed rate was 2.0 milliliters per minute, and a 3% palladium/carbon catalyst was employed.

TABLE 4

| Example | Catalyst Wt | HMD (% HMD) Wt | Wt BuO | % BuO | % BuOH | 3BHMD | TBHMD | TBHMD+1 | TBHMD+2 |
| --- | --- | --- | --- | --- | --- | --- | --- | --- | --- |
| 20 | 30 g | 174 (100) | 432 | 0.36 | 1.68 | 0.22 | 88.03 | 2.95 | 4.65 |
| 21 | 30 g | 174 (100) | 432 | 2.51 | 0.88 | 0.70 | 87.08 | 3.45 | 2.12 |
| 22 | 30 g | 174 (100) | 540 | 2.80 | 5.92 | 0.24 | 80.76 | 2.38 | 4.34 |
| 23 | 30 g | 218 (79.8) | 670 | 5.70 | — | — | 81.91 | 5.25 | 1.18 |
| 24 | 15 g | 197 (88.5) | 432 | 1.03 | 0.21 | — | 91.54 | 4.39 | 0.36 |
| 25 | 30 g | 218 (88.5) | 501 | 0.32 | 0.10 | — | 93.02 | 4.01 | 1.44 |
| 26 | 30 g | 218 (88.5) | 501 | 2.83 | 0.60 | — | 92.00 | 1.67 | 1.85 |
| 27 | 30 g | 197 (88.5) | 432 | 0.73 | 0.30 | 0 | 94.50 | 1.29 | 2.24 |
| 28 | 30 g | 197 (88.5) | 432 | 2.74 | 2.48 | 0 | 91.30 | 1.41 | — |

COMPARATIVE EXAMPLES 1A-14A

The indicated quantities of hexamethylenediamine (HMD) were dissolved in 75 milliliters of ethanol except that example 11A was a continuation of example 10A in which 50 milliliters of the reaction medium was drained from the autoclave before the addition of 9 grams butyraldehyde in 21 milliliters of ethanol. Example 12A was a continuation of example 11A in which 65 milliliters were drained from the reactor prior to the addition of 9 grams butyraldehyde in 31 milliliters of ethanol. Example 9A employed 57.6 grams of butyraldehyde in 180 milliliters of ethanol. Temperatures and pressures, the amount of hexamethylenediamine and the feed rate of butyraldehyde as well as product composition are shown on the following table. Raney nickel catalyst was employed.

TABLE 5

| Example | g HMD | Press. (psig H₂) | Press. (kg/cm²) | Temp. (°C.) | BuO Feed-Rate (mls/min) | % BuOH | % MBHMD | % DBHMD | % 3BHMD | % TBHMD |
| --- | --- | --- | --- | --- | --- | --- | --- | --- | --- | --- |
| 1A | 11.6 | 200 | 130 | 25 | 2 | ~0 | Typical condensation products | | | |
| 2A | 11.6 | 400 | 271 | 50 | 2 | 38.0 | — | 27.4 | 24.0 | 2.4 |
| 3A | 11.6 | 300 | 260 | 40 | 2 | 35.0 | 5.3 | 31.7 | 9.9 | 0.8 |
| 4A | 5.8 | 300 | 200 | 40 | 2 | 45.0 | 16.1 | 27.7 | 3.2 | — |
| 5A | 11.6 | 500 | 341 | 80 | 1 | 44.5 | — | 18.0 | 25.3 | 2.7 |
| 6A | 11.6 | 500 | 341 | 80 | 2 | 32.9 | — | 31.7 | 25.5 | 1.7 |
| 7A | 11.6 | 500 | 341 | 80 | 2 | 25.3 | — | 35.2 | 21.5 | 1.2 |
| 8A | 11.6 | 500 | 341 | 80 | 1 | 20.9 | — | 32.4 | 18.1 | 1.0 |
| 9A | 11.6 | 500 | 341 | 80 | 2 | 49.9 | 0.1 | 17.3 | 12.8 | 1.0 |
| 10A | 11.6 | 500 | 341 | 80 | 2 | 34.5 | — | 28.2 | 25.9 | 2.4 |
| 11A | — | — | — | — | 2 | 47.7 | — | 8.2 | 28.9 | 6.5 |
| 12A | — | — | — | — | 2 | 62.8 | — | 0.6 | 15.9 | 16.3 |
| 13A | 5.8 | 500 | 341 | 80 | 2 | — | — | 24.2 | 44.8 | 4.3 |
| 14A | 5.8 | 500 | 341 | 90 | 2 | — | — | 35.5 | 44.0 | 2.7 |

By "typical condensation products" in Table 5 is meant unmeasured but not atypical in appearance.

Modifications will be obvious to those skilled in the art.

I claim:

1. A process for the production of tetrabutylhexamethylenediamine from butyraldehyde and hexamethylenediamine comprising continuously reacting controlled amounts of butyraldehyde with hexamethylenediamine in the presence of a catalyst selected from the group consisting of platinum and palladium at a pressure of 300-500 psig and a temperature of 70°-90° C.

2. The process of claim 1 wherein the catalyst is platinum.

3. The process of claim 1 wherein the catalyst is palladium.

4. The process of claim 1 conducted at a pressure of about 500 psig.

5. The process of claim 1 conducted at a temperature of 80°-90° C.

6. The process of claim 1 wherein the reactants are dissolved in ethanol.

7. The process of claim 1 wherein the reactants are not dissolved in a solvent.

* * * * *